(12) United States Patent
Gill et al.

(10) Patent No.: US 7,526,338 B1
(45) Date of Patent: Apr. 28, 2009

(54) IMPLANTABLE CARDIAC DEVICE FOR MONITORING DIASTOLIC HEART FAILURE AND METHOD OF OPERATION AND USE THEREOF

(75) Inventors: Jong Gill, Valencia, CA (US); Xiaoyi Min, Thousand Oaks, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 383 days.

(21) Appl. No.: 11/136,268

(22) Filed: May 23, 2005

(51) Int. Cl.
*A61N 1/365* (2006.01)
*A61B 5/02* (2006.01)

(52) U.S. Cl. .............................. 607/18; 607/23; 607/25

(58) Field of Classification Search ................ 600/509, 600/513, 485–486, 508, 526; 607/23, 6, 607/9, 17, 18, 25, 28
See application file for complete search history.

(56) References Cited

U.S. PATENT DOCUMENTS

| | | | | |
|---|---|---|---|---|
| 4,815,469 | A | 3/1989 | Cohen et al. ................ | 128/634 |
| 5,040,538 | A | 8/1991 | Mortazavi ................... | 128/633 |
| 5,454,838 | A | 10/1995 | Vallana et al. ................ | 607/19 |
| 5,496,351 | A | 3/1996 | Plicchi et al. ................ | 607/17 |
| 5,758,652 | A * | 6/1998 | Nikolic ....................... | 600/487 |
| 5,797,850 | A | 8/1998 | Archibald et al. ........... | 600/494 |
| 6,258,576 | B1 | 7/2001 | Richards-Kortum et al. | 435/172 |
| 6,277,078 | B1 * | 8/2001 | Porat et al. .................. | 600/486 |
| 6,438,408 | B1 * | 8/2002 | Mulligan et al. ............ | 600/510 |
| 6,480,733 | B1 | 11/2002 | Turcott ........................ | 600/516 |
| 6,512,953 | B2 | 1/2003 | Florio et al. ................. | 607/28 |
| 6,561,984 | B1 | 5/2003 | Turcott ........................ | 600/485 |
| 6,575,912 | B1 | 6/2003 | Turcott ........................ | 600/485 |
| 6,643,548 | B1 | 11/2003 | Mai et al. ..................... | 607/17 |
| 6,645,153 | B2 | 11/2003 | Kroll et al. .................. | 600/481 |
| 6,658,283 | B1 | 12/2003 | Bornzin et al. .............. | 600/510 |
| 6,658,289 | B2 | 12/2003 | Helland ........................ | 607/4 |
| 6,701,187 | B1 | 3/2004 | Bornzin et al. ............... | 607/14 |

(Continued)

FOREIGN PATENT DOCUMENTS

EP     1 348 463 A1    10/2003

(Continued)

OTHER PUBLICATIONS

Alexander, Walter, "*ARB Could Provide Protection from Arrhythmias*," Today in Cardiology (Website), (Jul. 2004), 2 pages, http://www.todayincardiology.com.

(Continued)

*Primary Examiner*—Carl H Layno
*Assistant Examiner*—Jessica Reidel

(57) ABSTRACT

An implantable cardiac device is used to measure one or more parameters relating to cardiac activity of a patient's heart, from which diastolic heart failure ("DHF") may be monitored and/or detected. These parameters are used to calculate ventricular isovolumetric relaxation time or a related time value. Heart conditions possibly having an influence on the ventricular isovolumetric relaxation time, other than heart conditions due to reduced compliance, may be detected and used to prevent an incorrect calculation of the ventricular isovolumetric relaxation time. The parameters may be measured and the relaxation time calculated multiple times over a period of time, which enables monitoring of the progression of change in the relaxation time. The relaxation time and the progression of change therein are indicators of DHF.

18 Claims, 9 Drawing Sheets

U.S. PATENT DOCUMENTS

| | | | |
|---|---|---|---|
| 6,810,284 B1 * | 10/2004 | Bradley | 600/510 |
| 7,192,399 B2 * | 3/2007 | Kjellstrom et al. | 600/485 |
| 7,204,798 B2 * | 4/2007 | Zdeblick et al. | 600/17 |
| 2002/0151938 A1 * | 10/2002 | Corbucci | 607/25 |
| 2003/0045909 A1 | 3/2003 | Gross et al. | 607/9 |
| 2003/0055461 A1 * | 3/2003 | Girouard et al. | 607/17 |
| 2003/0153837 A1 * | 8/2003 | McIntyre | 600/485 |
| 2003/0153952 A1 | 8/2003 | Auricchio et al. | 607/9 |
| 2003/0204145 A1 * | 10/2003 | Manolas | 600/513 |
| 2003/0216653 A1 * | 11/2003 | Poliac et al. | 600/500 |
| 2004/0002626 A1 | 1/2004 | Feld et al. | 600/37 |
| 2004/0015196 A1 | 1/2004 | Holmstrom et al. | 607/17 |
| 2005/0027323 A1 * | 2/2005 | Mulligan et al. | 607/18 |
| 2005/0182447 A1 * | 8/2005 | Schecter | 607/2 |
| 2006/0224190 A1 * | 10/2006 | Gill et al. | 607/3 |
| 2007/0100249 A1 * | 5/2007 | Torpo et al. | 600/526 |
| 2007/0100279 A1 * | 5/2007 | Bates | 604/103.1 |

FOREIGN PATENT DOCUMENTS

| | | |
|---|---|---|
| WO | WO 2004/008959 A1 | 1/2004 |

OTHER PUBLICATIONS

Bareiss, P. et al., "*Modifications in the Contraction and Relaxation of the Left Ventricle in Chronic Ischemic Cardiopathies. Study Using Equilibrium Angio-Scintigraphy*," Arch Mal Coeur Vaiss., vol. 81, No. 4 (1998)—Abstract.

Berne, Robert M. et al., *Cardiovascular Physiology* (Sixth Edition), pp. 68-69.

Bounhoure, JP et al., "*Heart Failure with Preserved Left Ventricular Function: Clinical, Echocardiographic, and Clinical Course Feature. Prognostic Factors*," Bull Acad Natl Med., vol. 186, No. 6 (2002)—Abstract.

Brecker, Stephen J D et al., "*Relation of Left Ventricular Isovolumic Relaxation Time and Incoordination of Transmittal Doppler Filling Patterns*," British Heart Journal, vol. 68, No. 6 (1992), pp. 567-573.

Bruch, C. et al., "*Tei-Index in Coronary Artery Disease—Validation in Patients with Overall Cardiac and Isolated Diastolic Dysfunction*," Z Kardiol, vol. 91, No. 8 (Jun. 2002)—Abstract.

Cohen, Todd J., MD et al., "*A Hemodynamically Responsive Antiachycardia System*," Circulation, vol. 82 (1990), pp. 394-406.

Covic, Adrian, et al., "*Haemodialysis Increases QTc Interval but not QTc Dispersion in ESRD Patients Wihout Manifest Cardiac Disease*," Nephrology Dialysis Transplantation, vol. 17 (2002), pp. 2170-2177.

Dogan, Abdullah, MD et al., "*Does Impaired Left Ventricular Relaxation Affect P Wave Dispersion in Patients with Hypertension?*," Annals of Noninvasive Electrocardiology, vol. 8, No. 3 (2003), pp. 189-193.

Harjai, Kishore J. et al., "*The Tei Index: A New Prognostic Index for Patients with Symptomatic Heart Failure*," J Am Soc Echocardiogr, vol. 15, No. 9 (2002), pp. 864-868.

ISSYS Integrated Sensing Systems Medical Products Overview, http://www.memsissys.com/html/medfamily.html., 2002.

Kaliuzhin, VV et al., "*Role of Left Ventricular Systolic and Diastolic Dysfunction in Clinical Manifestations of Chronic Heart Failure in Patients with Prior Myocardial Infarction*," Ter Arkh, vol. 74, No. 12 (2002)—Abstract.

Kawaguchi, Miho, MD et al., "*Combined Ventricular Systolic and Arterial Stiffening in Patients with Heart Failure and Preserved Ejection Fraction*," Circulation, vol. 107 (2003), pp. 714-720.

Kosmala, Wojciech et al., "*Intraventricular Dispersion of Diastolic Left Ventricular Inflow as a New Indicator of Diastolic Dysfunction in Patients with Hypertension or Coronary Artery Disease*," Polish Heart Journal, vol. L, No. 1 (1999)—Abstract.

Lonati, L.M. et al., "*Patterns of QT Dispersion in Athletic and Hypertensive Left Ventricular Hypertrophy*," Annals of Noninvasive Electrocardiology, vol. 9, No. 3 (2004), pp. 252-256.

Makowski, Karol et al., "*Heart Rate Variability Determines Left Ventricular Diastolic Function in Essential Hypertension*," Polish Heart Journal, vol. LVI, No. 6 (2002)—Abstract.

Saad, Eduardo B., MD, Cardiology—Diastolic Heart Failure, http://www.medstudents.com.br/cardio/cardio5.htm, 2000.

Spenser, Kirk T., MD et al., "*Diastolic Heart Failure—What Primary Care Physicians Need to Know*," Postgraduate Medicine, vol. 101, No. 1 (1997).

Summers RL et al., "*Differentiating Systolic from Diastolic Heart Failure Using Impedance Cardiography*," Acad Emerg Med., vol. 6, No. 7 (1999)—Abstract.

Voon, Wen-Chol et al., "*Role of Intraventricular Dispersion of Early Diastolic Filling in Indicating Left Ventricular Diastolic Dysfunction: Assessment by Color M-Mode Inflow Propagation Velocity*," Cardiology, vol. 95, No. 3 (2001), pp. 151-155.

* cited by examiner

IMPLANTABLE CARDIAC DEVICE FOR MONITORING DIASTOLIC HEART FAILURE AND METHOD OF OPERATION AND USE THEREOF

FIELD OF THE INVENTION

The present invention relates to implantable cardiac devices, and more particularly to implantable cardiac devices for the detection and/or monitoring of diastolic heart failure, and methods of operation and use thereof.

BACKGROUND OF THE INVENTION

Heart failure ("HF") refers to an increasingly ineffective heart, or a dysfunction in the pumping action of the heart due to the heart's inability to contract or relax properly. Typically, the lower chambers of the heart (ventricles) do not beat as efficiently as they do in a healthy heart. As heart failure progresses, the body attempts to compensate for it. In an attempt to improve pumping function, the heart increases its muscle mass in a process called remodeling. While the remodeled, enlarged heart does pump more blood initially, it eventually requires more oxygen than it can get, resulting in further damage. In addition, the walls of the remodeled heart stiffen, and pumping efficiency decreases.

HF can be caused by an abnormality in systolic function leading to a defect in the expulsion of blood, which is known as systolic HF; or by an abnormality in diastolic function leading to a defect in ventricular filling, known as diastolic HF ("DHF"). Diastole is the normal rhythmic relaxation and dilatation of the ventricles during which they fill with blood. Atrial contraction occurs near the end of diastole to assist ventricular filling. Systole is the rhythmic contraction of the heart, especially of the ventricles, by which blood is driven through the aorta and the pulmonary artery. The preload is the load present before contraction of the ventricles begins, and is provided by the venous return that fills the ventricle during diastole. In DHF, ventricular stiffness or reduced compliance leads to limitations on the use of preload reserve because of rapid increases in cardiac filling pressures at normal or slightly increased cardiac volume. These effects limit cardiac output and cause dyspnea during exercise. See, e.g., Eduardo B. Saad, Cardiology: Diastolic Heart Failure, http://www.medstudents.com.br/cardio/cardio5.htm, 2000.

Detecting and monitoring the progression of DHF is difficult. Preserved ejection fraction ("EF") might appear to be a good indicator of DHF. However, patients with DHF generally have a preserved ejection fraction ("EF") greater than 50%, which is considered to be in the range of normal cardiac condition. Hence, EF alone is not sufficient for determining DHF. Recent findings suggest that changes in end-systolic elastance, effective arterial elastance, and pressure-volume curve are good indicators of DHF. See, e.g., Miho Kawaguchi, Ilan Hay, Barry Fetics, and David A. Kass, Combined Ventricular Systolic and Arterial Stiffening in Patients With Heart Failure and Preserved Ejection Fraction: Implications for Systolic and Diastolic Reserve Limitations, Circulation, February 2003; 107: 714-720. However, obtaining these values using conventional techniques is difficult, often requiring complex procedures with special sensors and tools.

Treatments for HF include medications, surgical procedures, heart transplant, and electrical stimulation therapy. Various electrical stimulation therapies are practiced by implantable cardiac stimulation devices, some of which are capable of pacing the heart of a patient in single or dual chamber modalities. Some heart failure patients may be candidates for an implantable cardiac stimulation device to provide cardiac resynchronization therapy ("CRT"). CRT involves pacing in three chambers instead of one chamber pacing in the right ventricle or two chamber pacing in the right ventricle and right atrium. A CRT device paces the right atrium, the right ventricle, and the left ventricle. The goal of CRT therapy is to synchronize the right and left ventricles to improve the efficiency of the contraction. The CRT functionality can be provided in pacemakers and implantable cardioverter defibrillators ("ICDs") which have built-in pacemakers. Although conventional implantable cardiac devices such as pacemakers and ICDs monitor various parameters, they are unsuitable for determining DHF.

To make electrical stimulation therapy and other treatments of HF more effective, improvements in monitoring the progression of DHF and other HF conditions using implantable cardiac devices are desirable.

BRIEF SUMMARY

What is described herein is a system and method that advantageously calculate ventricular isovolumetric relaxation time, an indicator of DHF, with an implantable cardiac device. One or more cardiac signals may be used for the calculation, including an intracardiac electrogram ("IEGM"), and preferably a right ventricular tip electrogram ("RVT-EGM"), from any suitable lead configuration, and a left ventricular ("LV") pressure measurement. The present invention may even be used with implantable cardiac devices having conventional lead systems, with only the addition of a LV pressure measurement.

One embodiment is a method of monitoring a patient for diastolic heart failure with an implanted cardiac device, comprising obtaining with the implanted cardiac device a waveform indicative of left ventricular pressure of the patient over an early part of isovolumetric relaxation, prior to earliest probable mitral valve opening; determining in the implanted cardiac device a parameter of the waveform; and calculating an indication of diastolic heart failure from the waveform parameter.

Another embodiment is a method of monitoring a patient for diastolic heart failure with an implanted cardiac device, comprising obtaining with the implanted cardiac device at least one cardiac signal indicative of cardiac activity of the patient; calculating from the cardiac signal in the implanted cardiac device a ventricular isovolumetric relaxation time; obtaining an indication of a heart condition that is capable of influencing the ventricular isovolumetric relaxation time, other than reduced ventricular compliance; and calculating an indication of diastolic heart failure from the ventricular isovolumetric relaxation time and the heart condition indication.

DETAILED DESCRIPTION OF THE INVENTION, INCLUDING THE BEST MODE

An implantable cardiac device is used to monitor and/or detect various heart failure ("HF") conditions, including diastolic heart failure ("DHF"), based on measurements of the left ventricular ("LV") pressure and various other cardiac signals of a patient in the various phases of the cardiac cycle, including ventricular isovolumetric relaxation.

Ventricular isovolumetric relaxation is the fifth heart phase. As the ventricles relax and intraventricular pressures fall, the total energy of blood within the ventricles becomes less than the energy of blood in the outflow tracts. The aortic valve abruptly closes in response, which contributes to the second heart sound S2 (the pulmonic valve also abruptly closes just after the aortic valve and also contributes to the second heart sounds S2). Upon aortic valve closure, a small backflow of blood into the left ventricle occurs, resulting in the characteristic dicrotic notch in the aortic artery pressure tracing. Although left ventricular pressure decreases, the volume remains constant because both valves are closed. The volume of blood that remains in the left ventricle is called the end-systolic volume and is about 50 ml. The difference between the end-diastolic volume and the end-systolic volume is known as the stroke volume and is about 70 ml.

Figure 1:
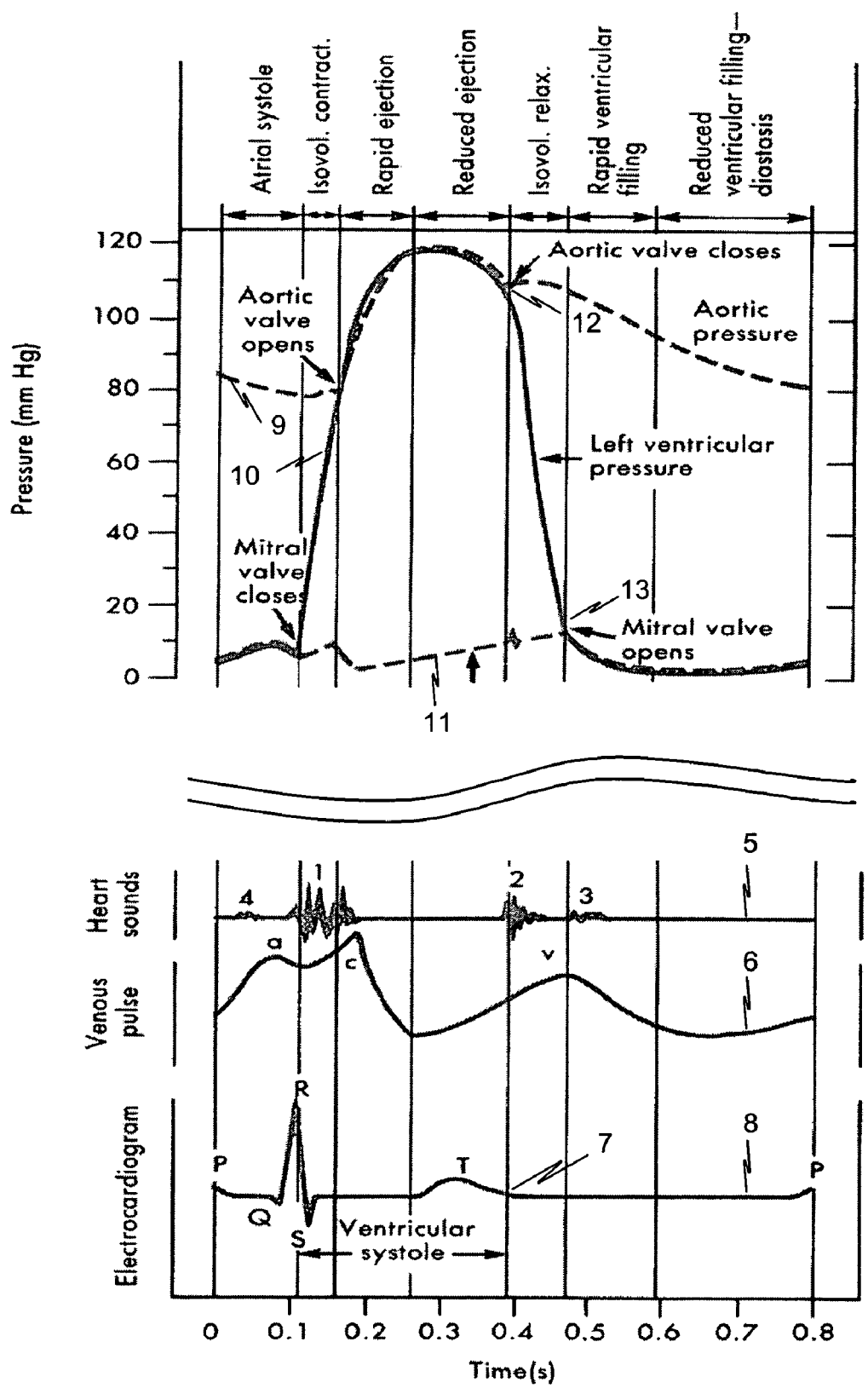
FIG. 1 is a set of graphs showing left atrial, aortic, and left ventricular pressure waveforms correlated in time with aortic flow, ventricular volume, heart sounds, venous pulse, and electrocardiogram waveforms for a complete cardiac cycle in the canine.

Diastolic heart failure is indicated by the ventricular isovolumetric relaxation time ("IVRT"), which is defined as the interval between aortic (aortic semilunar) valve closure and mitral (left atrioventricular) valve opening. Relaxation time can be better understood with reference to FIG. 1, which is reproduced from Robert M. Berne & Matthew N. Levy, Cardiovascular Physiology, Sixth Edition, 1992, pp. 68-69. FIG. 1 shows aortic pressure 9, left ventricular ("LV") pressure 10, and left atrial pressure 11, correlated in time with heart sounds 5, venous pulse 6, and a surface electrocardiogram ("ECG") 8 for a complete cardiac cycle in the canine. The ventricular isovolumetric relaxation time ("IVRT") corresponds to the interval from the end of the T wave to the return of LV pressure to baseline, and this time may be calculated to obtain an indication of DHF, and the progression of change in relaxation time may also be monitored to obtain an indication of DHF.

Observe from the LV pressure 10 and the surface ECG 8 that aortic valve closure 12, which correlates with heart sound 2 on the heart sounds waveform 5, coincides with the end 7 of the T wave segment of the surface ECG 8. Expansion of the ventricular tissue is manifest as a T-wave, which is separate from the QRS complex in which contraction of atrial muscle tissue is manifest by the generation of a P-wave and contraction of ventricular muscle tissue is manifest by the generation of an R-wave. Expansion of the atrial tissue usually does not result in a detectable signal.

Ventricular isovolumetric relaxation time is believed to be an indicator of heart failure, even in patients with preserved ejection fraction ("HF-1nEF"), because such patients have systolic-ventricular and arterial stiffening beyond that associated with aging, hypertension, or both; see Kawaguchi et al., supra. Systolic-ventricular and arterial stiffening is believed to play an important pathophysiological role by exacerbating systemic load interaction with diastolic function, augmenting blood pressure lability, and elevating cardiac metabolic demand under stress. Systolic-ventricular and arterial stiffening are believed to influence diastole by elevating systolic load to prolong relaxation, compromise filling, and raise end-diastolic pressure ("EDP"). Specifically, for HF-n1EF patients during hand grip exercise, relaxation time on average increases relative to a baseline non-DHF state; the relaxation time interval was about 59 msec for the controls, but increased to about 86 msec on average in DHF patients, according to Kawaguchi et al.

Unfortunately, relaxation time is not a consistently reliable indicator of DHF. The hallmark of DHF is impairment of relaxation, which can be affected by heart conditions other than reduced compliance. Some of these heart conditions are indicated by the electrical activity of the heart. A wide QRS complex, for example, may indicate dispersion of depolarization and can result in prolonged ventricular isovolumetric relaxation. A wide T wave may indicate dispersion of repolarization, which can also result in prolonged ventricular isovolumetric relaxation. Some of the conditions are mechanical, and can be detected in the LV pressure waveform itself. One such condition is dispersion of relaxation, a mechanical dissynchrony in which relaxation of the ventricles is not in synchrony even though the ventricles have normal compliance. The effect of dispersion of relaxation on the LV pressure waveform is to increase the apparent relaxation time. While the increased apparent relaxation time in this case is indicative of a heart abnormality, that abnormality is not DHF. Other indicia of heart failure conditions that may have an impact on the LV pressure waveform during ventricular isovolumetric relaxation include wide T wave interval, dispersion of T wave, and so forth.

Figure 2:
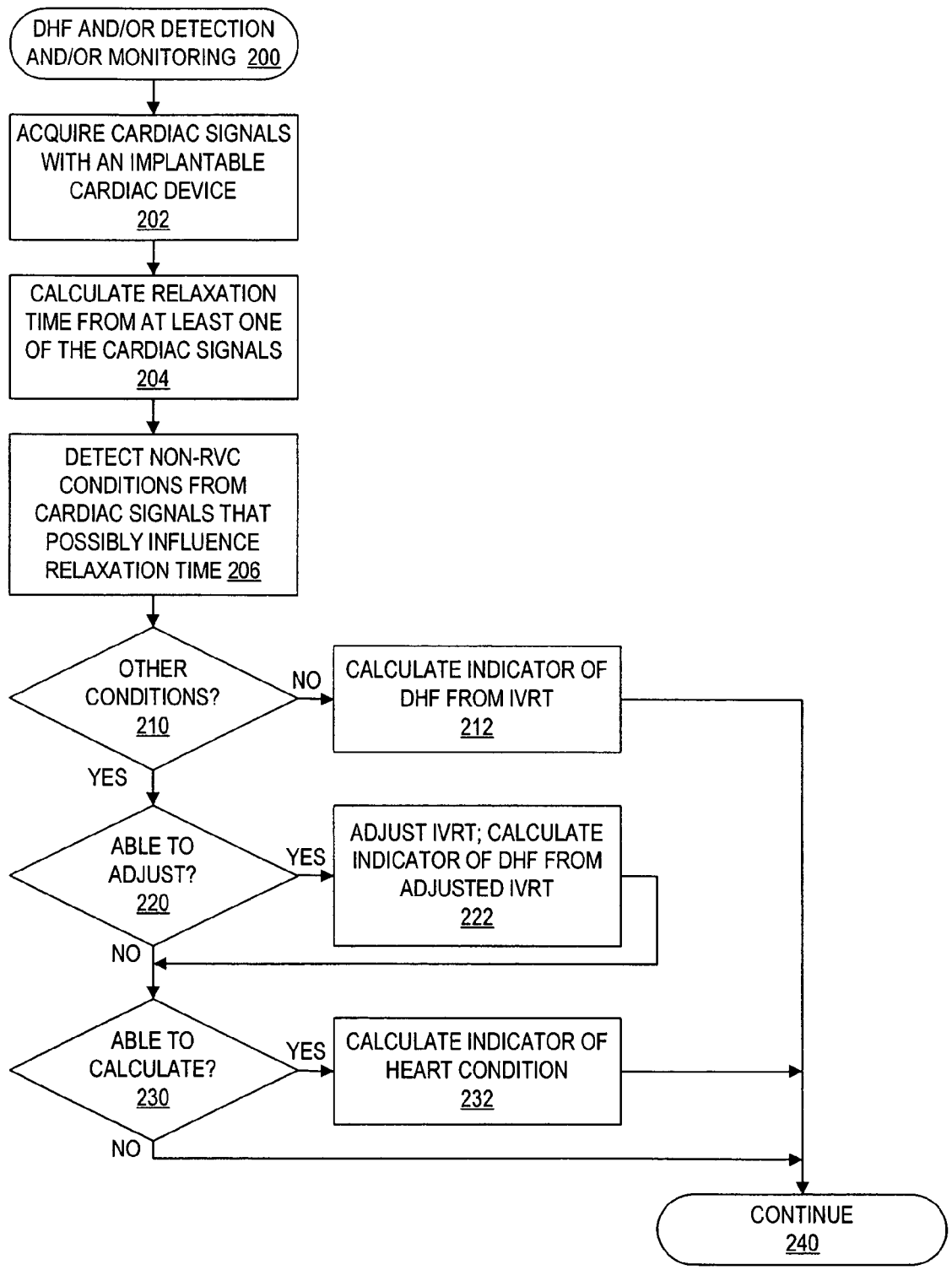
FIG. 2 is a flowchart that shows a process for detecting and/or monitoring diastolic heart failure, including correction for heart conditions other than reduced ventricular compliance.

FIG. 2 is a flowchart that shows a process 200 for detecting and/or monitoring DHF, including correction for heart conditions other than reduced ventricular compliance. Various cardiac signals including the LV pressure are acquired with an implantable cardiac device (block 202). The signals may relate to electrical, mechanical or chemical properties of the heart, including in particular properties that can affect various characteristics of the LV pressure during ventricular isovolumetric relaxation. The ventricular isovolumetric relaxation time IVRT is calculated using one or more of these cardiac signals, including preferably the LV pressure waveform (block 204). The cardiac signals are also used to detect heart conditions that can influence the ventricular isovolumetric relaxation time, other than reduced ventricular compliance (non-RVC conditions) (block 206). If no such conditions are found (block 210—no), an indicator of DHF is calculated from the ventricular isovolumetric relaxation time (block 212) and the process continues (block 240) without any need to adjust the IVRT measurement from which the DHF indicator is calculated. Alternatively, the DHF indicator is calculated with a high confidence notation. However, if a non-RVC condition that can influence the relaxation time are found (block 210—yes), a determination is made as to whether the IVRT measurement can be adjusted based on the detected condition. If an adjustment can be made (block 220—yes), the IVRT measurement is adjusted and an indicator of DHF is calculated from the adjusted IVRT (block 222). Otherwise (block 220—no), the IVRT measurement is not used for calculation of the DHF indicator. Alternatively, the DHF indicator is calculated with a low confidence notation. If the detected non-RVC condition is such that an indication of heart failure can be calculated from the cardiac signals (block 230—yes), the indicator of HF is calculated (block 232) and processing continues as desired (block 240). Otherwise (block 230—no), processing continues without calculation of the HF indicator.

The relaxation time and progression of change thereof may be used in various ways, depending on the type of implantable cardiac device. Preferably, the relaxation time and the progression of change thereof is calculated by the implantable cardiac device. Where the implantable cardiac device is used to monitor the ventricular isovolumetric relaxation time, the relaxation time results may be interrogated using the communications capability of the implantable cardiac device and communicated to an external processor in any suitable manner for further analysis. Where the implantable cardiac device is used as a DHF monitor, a DHF indicator is calculated by the implantable cardiac device, which may communicate an alarm signal to an external device when DHF is detected. Additionally or alternatively, the implantable cardiac device may automatically transmit the relaxation time and DHF results to an external device, or the external device may interrogate the implantable cardiac device for the results. Where the implantable cardiac device is used to treat DHF by electrical stimulation therapy, the implantable device itself may calculate a DHF indicator from the relaxation time and/or the progression of change in the relaxation time and adjust the stimulation therapy based on the calculated progression of change. Especially when used for DHF therapy, preferably the implantable cardiac device also detects non-RVC conditions that can influence the relaxation time, and either adjusts the IVRT measurement for the detected condition, or discards the IVRT measurement as being unreliable. Alternatively or additionally, the implantable cardiac device may store digitized waveforms and communicate this information to an external system for further processing, or may detect and store various parameters of the cardiac signals, such as the ending time of the T wave and the time of return to baseline of LV pressure, and communicate this information to an external system for further processing.

Implantable Cardiac Device

An implantable cardiac device is any implantable device capable of measuring one or more cardiac signals such as LV pressure, and preferably both LV pressure and an IEGM. An implantable cardiac device may also be capable of measuring non-cardiac signals, if desired. Preferably, an implantable cardiac device has sufficient processing capability to calculate IVRT from cardiac signals, calculate an indicator of DHF from the IVRT, and detect non-RVC conditions that may interfere with DHF monitoring and/or detection. The term implantable cardiac device also includes implantable devices that are also capable of dispensing medications for the heart and providing electrical stimulation therapy to the heart. Implantable cardiac devices may, if desired, contain sufficient memory to store waveforms and/or date over extended periods. Implantable cardiac devices may, if desired, have a capability of communicating data and/or programming externally, so that data may be transferred for external processing, and so that the device may be externally reprogrammable as appropriate in view of trends in the data, changes in parameters and coefficients, changes in data processing algorithms, to accommodate new treatment regimens, and so forth. Pacemakers, ICD's and CRT devices are all implantable cardiac devices having additional capabilities.

Figure 3:
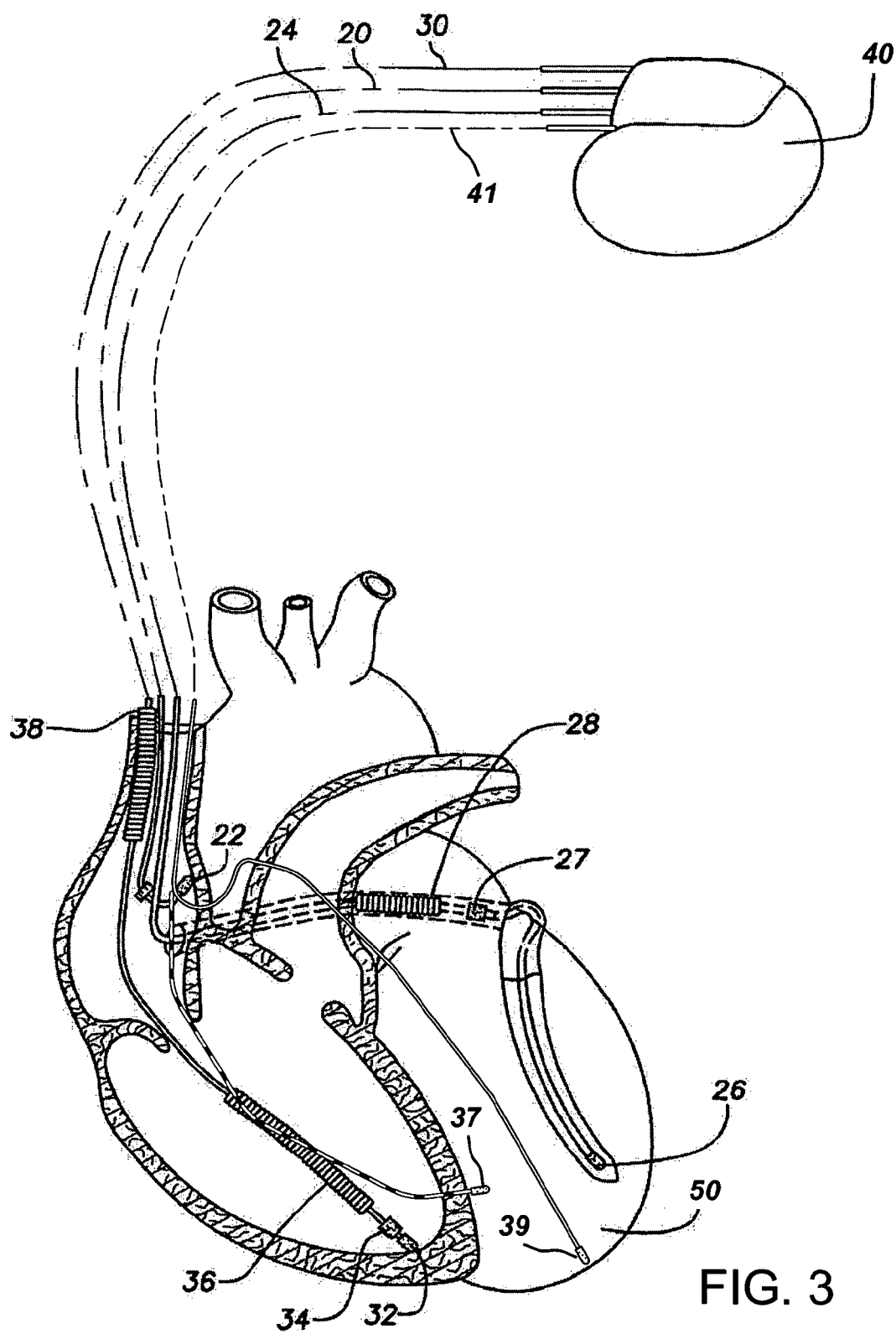
FIG. 3 is a simplified, partly cutaway view showing a multi-chamber implantable cardiac device in electrical communication with four leads implanted into a patient's heart.

FIG. 3 is a simplified, partly cutaway view showing a particular type of implantable cardiac device, an implantable stimulation device 40 that not only monitors DHF and various HF conditions, but is also suitable for delivering multi-chamber stimulation and shock therapy and for adjusting the stimulation therapy based on the results of the monitoring. The device of FIG. 3 is merely illustrative, and many other types of implantable cardiac devices may be modified to detect and/or monitor DHF as described herein. The stimulation device 40 is in electrical communication with a patient's heart 50 by four implanted leads 20, 24, 30 and 41. An illustrative stimulation device lacking LV pressure sensing capabilities but otherwise suitable for use as the stimulation device 40, along with methods of operation thereof and use thereof, are described in detail in U.S. Pat. No. 6,512,953, issued Jan. 28, 2003 to Florio et al., which hereby is incorporated herein in its entirety by reference thereto.

To sense atrial cardiac signals and to provide right atrial chamber stimulation therapy, the stimulation device 40 is connected to an implantable right atrial lead 20 having an atrial tip electrode 22, which typically is implanted in the patient's right atrial appendage.

To sense left atrial and ventricular cardiac signals and to provide left-chamber stimulation therapy, the stimulation device 40 is connected to a coronary sinus lead 24 designed for placement in the coronary sinus region via the coronary sinus ostia so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals, and to deliver left ventricular stimulation therapy using at least a left ventricular tip electrode 26, left atrial stimulation therapy using at least a left atrial ring electrode 27, and shocking therapy using at least a left atrial coil electrode 28.

LV pressure is measured with a left ventricular pressure sensor, which may be implanted in various ways. FIG. 3 shows a pressure sensor lead 41, an illustrative placement of a pressure sensor 37 through the ventricular septum, and an alternative illustrative placement of a pressure sensor 39 through the atrium septum. To place the pressure sensor 37, for example, one may place the lead with the sensor 37 attached at the tip through the ventricular septum from the right ventricle into the left ventricle. To place the pressure sensor 39, for example, one may place the lead with the sensor 39 attached at the tip through the atrial septum from the right atrium to the left atrium, and then into the left ventricle through the mitral valve. Suitable LV pressure sensors and measurement circuitry are well known in the art, and may be integrated into known implantable cardiac devices without undue experimentation. Suitable LV pressure sensors are well known in the art, including those of Integrated Sensing Systems, Inc. of Ypsilanti, Mich.; see http://www.mems-issys.com/html/medfamily.html.

The stimulation device 40 is further connected to an implantable right ventricular lead 30 having a right ventricular tip electrode 32, a right ventricular ring electrode 34, a right ventricular ("RV") coil electrode 36, and a superior vena cava ("SVC") coil electrode 38. Typically, the right ventricular lead 30 is transvenously inserted into the heart 50 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals such as the RVT-EGM, and delivering stimulation in the form of pacing and shock therapy to the right ventricle.

Figure 4:
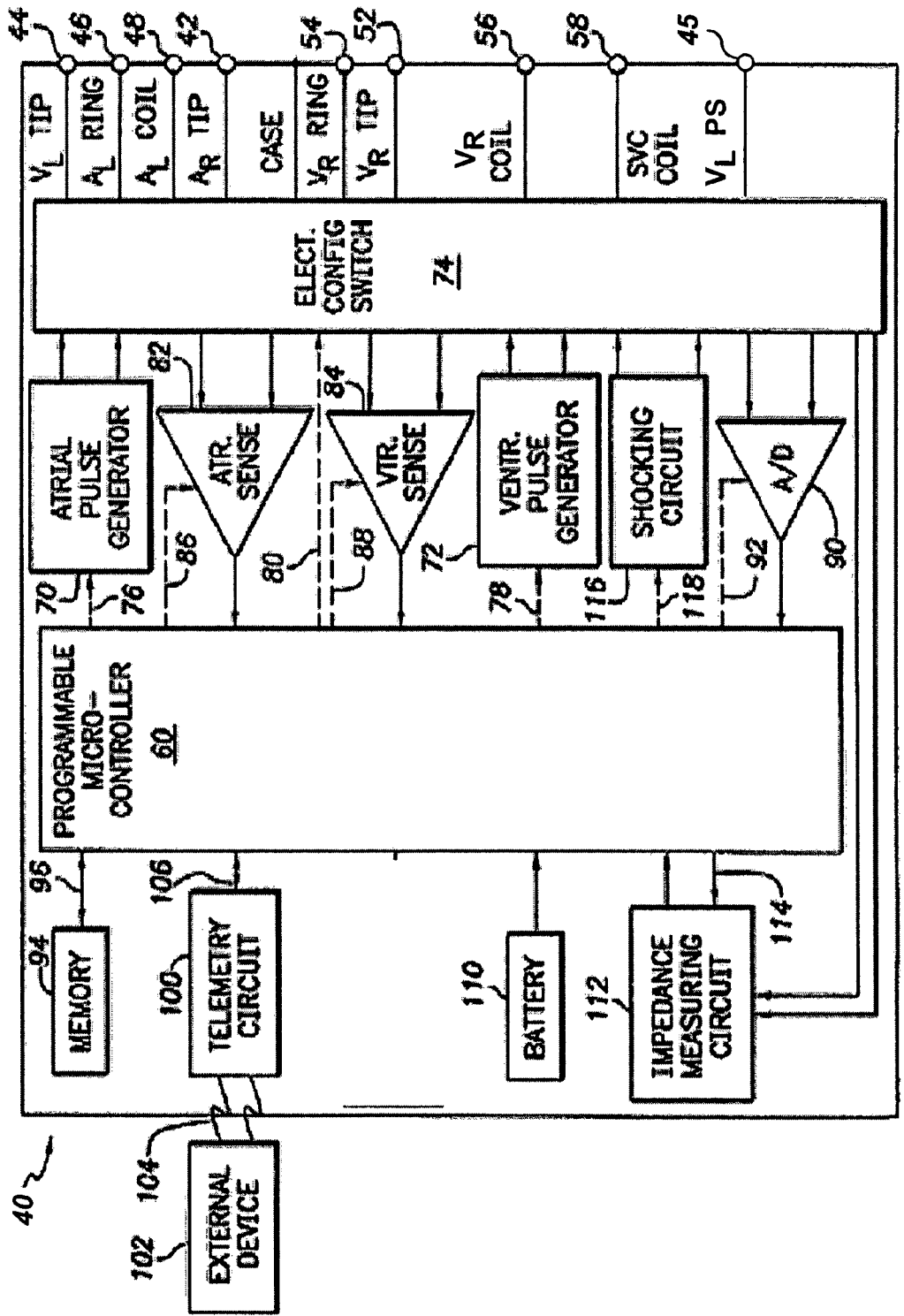
FIG. 4 is a functional block diagram showing the major functional circuits of the cardiac device of FIG. 3.

FIG. 4 is a block diagram of illustrative major functional circuits of the stimulation device 40. In addition to treating both fast and slow arrhythmias with stimulation therapy, including cardioversion, defibrillation, and stimulation, the simulation device 40 calculates various DHF and HF conditions, and adjusts the stimulation therapy based on the calculations. While a particular multi-chamber device is shown, this is for illustration purposes only. Appropriate circuitry may be duplicated, eliminated, or disabled in any desired combination to provide a device capable of treating the appropriate chamber(s) with cardioversion, defibrillation and/or pacing stimulation.

The stimulation device 40 includes a housing which may be programmably selected to act as the return electrode for the unipolar modes. The housing 40 may further be used as a return electrode alone or in combination with one or more of the coil electrodes 28, 36, or 38, for shocking purposes.

The stimulation device 40 further includes a connector (not shown) having a plurality of terminals 42, 44, 45, 46, 48, 52, 54, 56 and 58. To enable right atrial sensing and stimulation, the connector includes a terminal 42 for connection to the right atrial tip electrode 22. To enable left chamber sensing, pacing and/or shocking, the connector includes terminals 44, 46, and 48 for connection to the left ventricular tip electrode 26, the left atrial tip electrode 27, and the left atrial coil electrode 28, respectively. To enable a left ventricular pressure measurement, the connector includes a terminal 45 for connection to the left ventricular pressure sensor 43. To enable right chamber sensing, pacing and/or shocking, the connector includes terminals 52, 54, 56, and 58 for connection to the right ventricular tip electrode 32, right ventricular ring electrode 34, the right ventricular coil electrode 36, and the SVC coil electrode 38, respectively.

Figure 7:
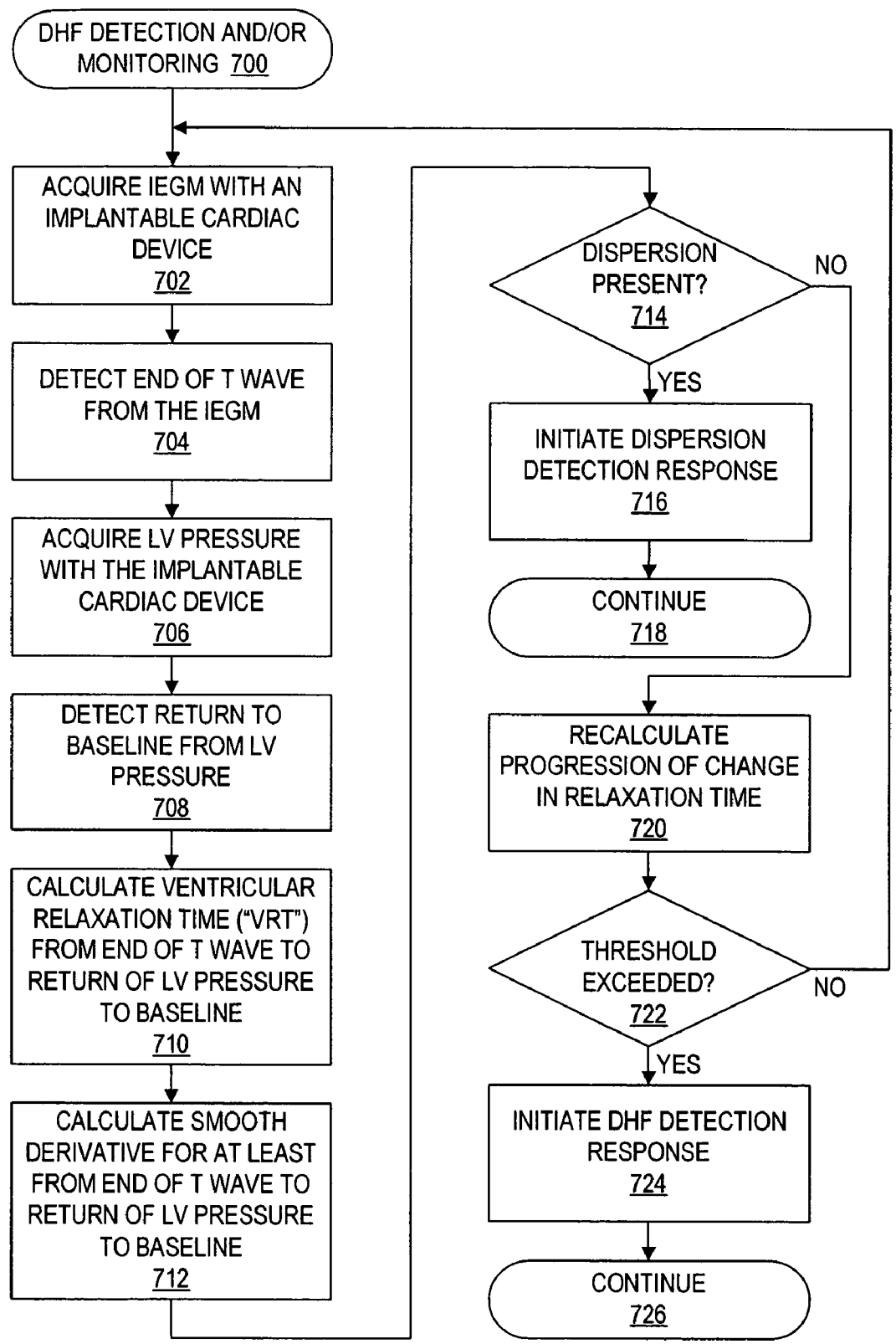
FIG. 7 is a flowchart showing operation of the implantable cardiac device of FIG. 3 and FIG. 4 to monitor and/or detect DHF, including correction for dispersion of relaxation.

A processor which preferably is a programmable microcontroller 60 with associated memory 94, but which may be any type of processor having programmable elements, fixed programmed elements, logic circuit elements, or combinations thereof, controls the acquisition of cardiac data as well as the various modes of stimulation therapy. The microcontroller 60 directs the execution of a variety of stimulation and measurement events, including a method for calculating relaxation time and monitoring the progression of change therein over time as shown in FIG. 7.

A switch bank 74 includes a plurality of switches for connecting the desired electrodes to appropriate I/O circuits under control of the microcontroller 60, thereby providing complete electrode programmability. An atrial pulse generator 70 and a ventricular pulse generator 72 generate pacing stimulation pulses under control of the microcontroller 60 for delivery by the right atrial lead 20, the right ventricular lead 30, and/or the coronary sinus lead 24 via the switch bank 74. Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. The atrial and ventricular sensing circuits 82 and 84 receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84. For arrhythmia detection, the stimulation device 40 utilizes the atrial and ventricular sensing circuits 82 and 84 to sense cardiac signals, for determining whether a rhythm is physiologic or pathologic.

Cardiac signals are also applied to the inputs of an analog-to-digital (A/D) data acquisition system 90. The data acquisition system 90 is configured to acquire intracardiac electrogram signals and the LV pressure signal, convert the raw analog data into digital signals, and store the digital signals for contemporaneous or subsequent processing and/or telemetric transmission to an external device 102. The data acquisition system 90 is connected to the right atrial lead 20, the coronary sinus lead 24, and the right ventricular lead 30 through the switch bank 74 to sample cardiac signals across any pair of desired electrodes. The data acquisition system 90 is also connected to the pressure sensor lead 41 through the switch bank 74 and the terminal 45 to sample LV pressure at the pressure sensor 43. The LV pressure signal at the terminal 45 and the right ventricular tip signal at the terminal 52 are used to determine relaxation time.

The microcontroller 60 communicates with a memory 94, which contains stored program components and data for the various functions carried out by the device 40. The device 40 may have an ability to sense and store a large amount of data from, for example, the data acquisition system 90. The stored data may be contemporaneously accessed by the device 40 for real time calculations and dynamic modification of therapy, or may be accessed later for subsequent analysis to guide the programming of the device 40. The programs and data of the device 40 may be non-invasively accessed by an external device 102 through a telemetry circuit 100 in telemetric communication with the external device 102. The telemetry circuit 100 advantageously allows intracardiac electrograms and status information relating to the operation of the device 40 to be sent to the external device 102 through the established communication link 104.

The stimulation device 40 may also include a power source such as a battery 110 to provide operating power, an impedance measuring circuit 112 which is responsive to a control signal 114 for a variety of applications, and a shocking circuit 116 responsive to a control signal 118.

Determination of the Ventricular isovolumetric Relaxation Time

An implantable cardiac device is used to measure one or more parameters from which diastolic heart failure ("DHF") may be monitored and/or detected. Two useful time parameters are the time of ending of the patient's T wave, and the time of return to baseline of the patient's left ventricular ("LV") pressure. Ventricular isovolumetric relaxation extends from aortic valve closure, which is indicated by the end of the T wave, to mitral valve opening, which is indicated by the return of LV pressure to baseline. The baseline value may vary dynamically or may be set at a pre-defined threshold, as desired. These two time parameters are used to calculate the ventricular isovolumetric relaxation time, which is believed to be an indicator of heart failure even in patients with preserved ejection fraction. Preferably the time parameters are measured for multiple heart beats over a period of time, which enables not only calculation of the IVRT for each heart beat, but also calculation of the progression of change in the relaxation time. The relaxation time and the progression of change thereof are indicators of DHF.

A right ventricular tip electrogram ("RVT-EGM") such as obtainable from the right ventricular lead 30 in the stimulation device 40 (FIG. 3) may be used in a similar manner as the ECG of FIG. 1 to obtain the end of the T wave. The RVT-EGM may be obtained using, for example, a unipolar lead. The unipolar lead is a commonly used type of sensing lead that includes a single electrode at its tip, and detects electrical voltage differentials between the electrode and the device itself. Another commonly employed type of sensing lead which may be used is the bipolar lead wherein the lead includes two electrodes mounted near its tip to detect electrical voltage differentials therebetween. In addition to the RVT-EGM, other types of intracardiac electrogram ("IEGM") configurations may be used as well, such as, for example, the right atrial tip-to-can electrogram ("RAT-EGM").

The end of the T wave may be determined by any suitable mathematical technique using digitized samples of the RVT-EGM waveform. One suitable technique is to find the point at which the amplitude reaches the pre-R baseline value.

The return of LV pressure to baseline may be detected by comparing the LV pressure to a baseline value. The baseline value may be determined dynamically on the basis of the LV pressure after ventricular isovolumetric relaxation for prior heart beats, or established statically by assigning a pre-defined threshold value.

Alternatively, the baseline return of the LV pressure may be determined by any suitable mathematical technique using digitized samples of the LV pressure waveform. One suitable technique is to trace back the LV pressure to find the point where it deviates from the baseline. In other words, determine some baseline point well beyond the end of the T wave but before the beginning of the next P wave, and then trace back to find the point which deviates from the baseline.

Figure 5:
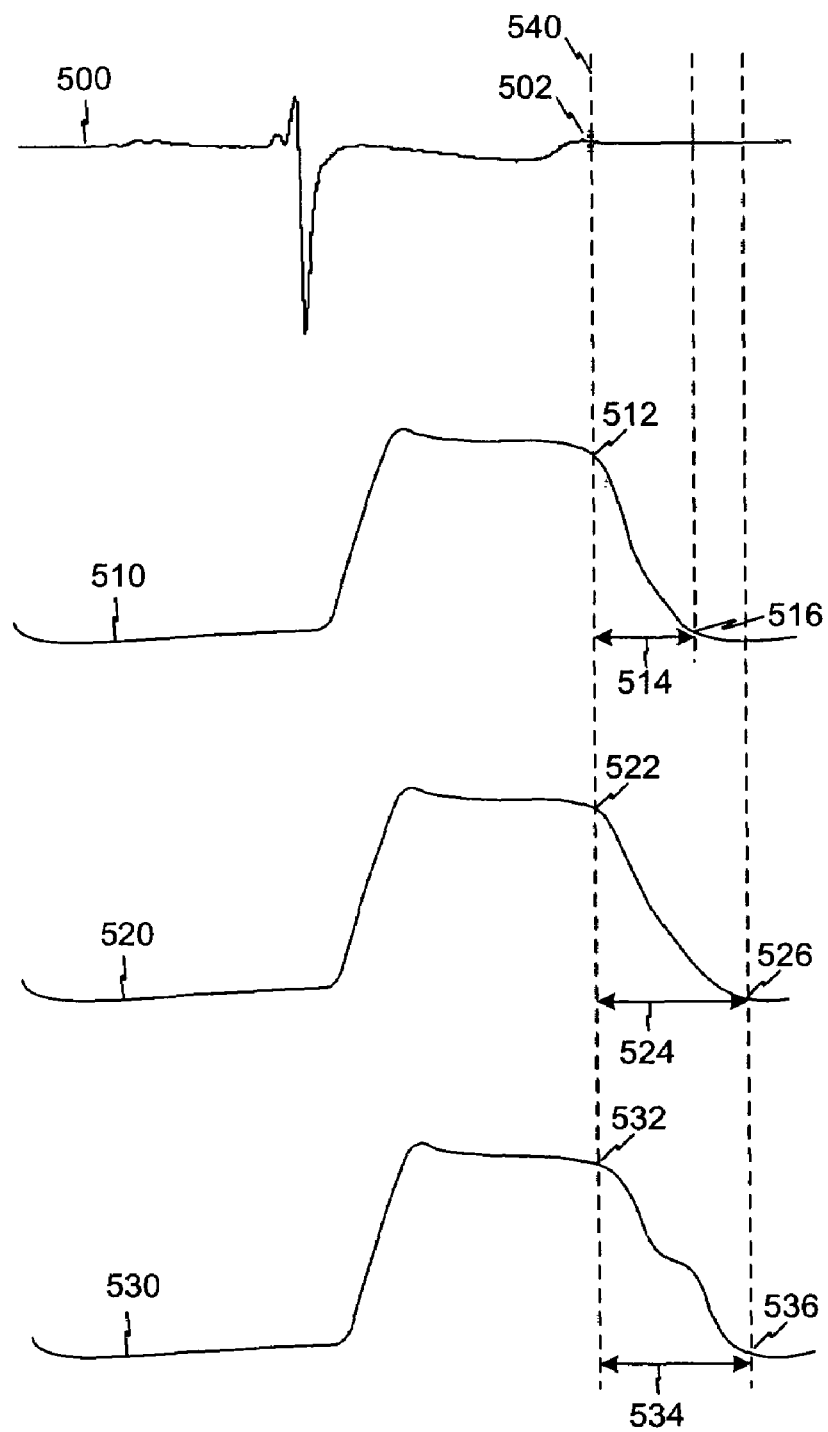
FIG. 5 is a graph showing waveforms for a right ventricular tip ("RVT") EGM and for left ventricular ("LV") pressure for three different heart conditions, correlated in time for a complete cardiac cycle.

FIG. 5 is a graph showing a waveform 500 for a right ventricular tip ("RVT") EGM, and three left ventricular ("LV") pressure waveforms 510, 520 and 530 for three different heart conditions, correlated in time for a complete cardiac cycle. The waveforms 500 and 510 are from canine data with a sampling frequency of 1024 Hz. It will be appreciated that the waveforms of FIG. 5 are similar to analogous waveforms in FIG. 1, except that the RVT-to-case unipolar EGM is used instead of a surface ECG. The vertical line 540 in FIG. 5 shows the start of the rapid decline in LV pressure after aortic valve closure, which is indicated by the end 502 of the T wave. This situation allows reliable detection from an implantable cardiac device of the beginning of ventricular isovolumetric relaxation. The end of ventricular isovolumetric relaxation at mitral valve opening may be subsequently obtained by scanning the remainder of the LV pressure waveform to find the baseline return. The baseline return of the LV pressure waveforms 510, 520 and 530 is indicated at 516, 526 and 536 respectively. The IVRTs 514, 524 and 534 for the respective waveforms 510, 520 and 530 are calculated as the differences between these times.

Ventricular isovolumetric relaxation times may be used in different ways to identify DHF. One approach is to compare the IVRT determination with an empirically derived absolute value. Another approach is to monitor for a substantial increase from a baseline value to diagnose DHF. Baseline value may be determined by measuring IVRT periodically, such as, for example, every two hours, and obtaining the average of a number of the previous measured IVRT's. This may be considered to be a moving average IVRT. A substantial increase from baseline may be defined as the exceeding of a pre-determined threshold value by the moving average IVRT.

While the end of the T wave as obtained from a RVT-EGM may be used to detect the start of ventricular isovolumetric relaxation, other measurements may be used as well. Other suitable measurements include detection of the dicrotic notch from waveform analysis of the aortic pressure, detection of the heart sounds S2 from an acoustic sensor, waveform analysis of the LV pressure to detect a change from a slow decline to a rapid decline, and detection of a discontinuity or blip in a left atrial pressure measurement. In addition, impedance, ultrasound, and aorta bloodflow measurements may be used to detect aortic valve closure, hence the start of ventricular isovolumetric relaxation. Moreover, the start of ventricular isovolumetric relaxation may be estimated from a percentage decline in LV pressure from the peak LV pressure. These techniques may be used individually, or two or more techniques may be used together to improve the accuracy and confidence of the start time determination. The heart sounds S2, for example, may be difficult to identify in a patient suffering from stenosis, regurgitation, or systolic murmur, and the T wave may be used to assist in the identification. The dicrotic notch may be very clearly identifiable in some patients and may be relied upon to detect the start of ventricular isovolumetric relaxation in those patients, whereas the dicrotic notch may be indistinct or altogether absent in other patients and would be of little or no use.

While the baseline return of LV pressure as obtained from the LV pressure waveform may be used to detect the end of ventricular isovolumetric relaxation, other measurements may be used as well. Other suitable measurements include detection of the heart sounds S3 from an acoustic sensor, and detection of a change in the LV pressure from a rapid decline to a slow decline. These techniques may be used individually, or two or more techniques may be used concurrently to improve the accuracy and confidence of the end time determination.

Effects on IVRT of Dispersion of Relaxation

Because heart conditions other than ventricular stiffness or reduced compliance affect relaxation time, relaxation time alone is not a consistently reliable indicator of DHF. Some of these heart conditions are apparent in electrical measurements of the heart, some are apparent in the mechanical measurements, and some are apparent in chemical measurements. An example of a mechanical condition is dispersion of relaxation, a mechanical dissynchrony in which relaxation of the ventricles is not in synchrony even though the individual ventricles have normal compliance.

The effect of dispersion of relaxation on the LV pressure waveform is to increase the apparent relaxation time. The vertical line 540 in FIG. 5 shows the start of the rapid decline in LV pressure after aortic valve closure, of which the end 502 of the T wave is indicative. The end of ventricular isovolumetric relaxation at mitral valve opening is identified by the return to baseline of the LV pressure waveforms 510, 520 and 530, as is indicated at 516, 526 and 536 respectively. The IVRT 514, 524 and 534 for the respective waveforms 510, 520 and 530 are calculated as the differences between these times. A comparison of the relaxation times 514, 524 and 534 reveals that relaxation times 524 and 534 are roughly equal, while relaxation time 514 is shorter. The relative relaxation times would suggest that the heart producing waveform 510 is normal while the hearts producing waveforms 520 and 530 suffer from DHF. While this conclusion would be appropriate for the hearts producing waveforms 510 and 520, it would not be appropriate for the heart producing waveform 530. The irregularity in the waveform 530 between points 532 and 536 is indicative of dispersion of relaxation, so that while the heart that produces waveform 530 suffers from HF, it may not suffer from DHF.

An illustrative technique for detecting dispersion of relaxation is to calculate the smooth first derivative of the LV pressure over at least the interval of ventricular isovolumetric relaxation, and identify the lowest value of the smooth first derivative over that interval. The smooth first derivative may also be calculated throughout each heart beat and used for other purposes as well. The smooth first derivative, which is in effect a low pass filter, is obtained by averaging the change in pressure per change in time, or dP/dT, over multiple samples. If the sampling rate of the LV pressure waveform is 250 Hz, for example, a sample is taken every 4 ms and dP/dT may be calculated over any desired interval, such as, illustratively, 12 ms (3 samples), 16 ms (4 samples), 20 ms (5 samples), or even longer intervals. Alternatively, instantaneous first derivatives may be calculated and averaged.

Figure 6:
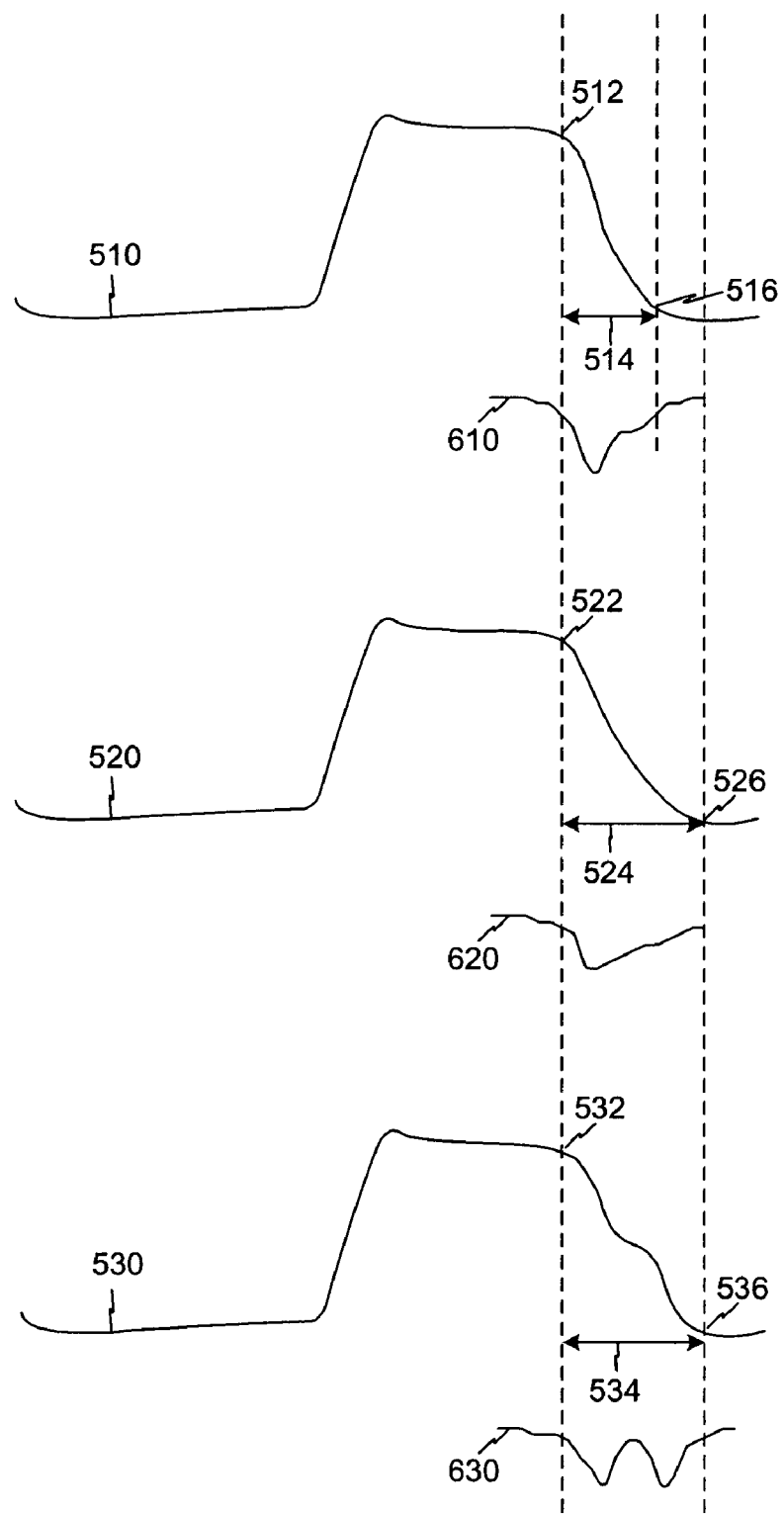
FIG. 6 is a graph showing smooth derivatives correlated in time with their respective isovolumetric relaxation intervals from the waveforms shown in FIG. 5.

FIG. 6 is a graph showing smooth derivatives of LV pressure 610, 620 and 630 during ventricular isovolumetric relaxation, correlated in time with their respective ventricular isovolumetric relaxation intervals from the waveforms 510, 520 and 530. A relatively large negative peak in the smooth first derivative 610 along with a short relaxation time indicates an absence of DHF. On the other hand, a relatively small negative peak in the smooth first derivative 620 along with a long relaxation time indicates diastolic heart failure ("DHF"). However, if multiple negative peaks occur in the smooth first derivative, as shown in the trace 630, along with a long relaxation time, a dispersion of relaxation would be indicated. Note that the long relaxation time alone would incorrectly indicate DHF.

FIG. 7 is a flowchart showing in detail an illustrative DHF detection and/or monitoring method 700, which may be implemented as a stored program in the memory 94 of the microcontroller 60. The method 700 includes acquiring an IEGM measurement, preferably a RVT-EGM measurement, with the implantable cardiac device (block 702), and detecting the end of the T wave from the IEGM measurement (block 704). The method 700 further includes acquiring a LV pressure measurement with the implantable cardiac device (block 706), and detecting the return to baseline of the LV pressure from the LV pressure measurement (block 708). If desired, the detected ending time of the T wave may be used as a trigger to begin detection for the return to baseline of the LV pressure. Once the two parameters have been measured, the method resumes with calculating the ventricular relaxation time based on the time interval from the end of the T wave to return of the LV pressure to baseline (block 710).

The newly calculated ventricular relaxation time is checked for influences of non-RVC conditions that may impact IVRT, such as, for example, dispersion of relaxation. One technique involves calculating the smooth first derivative over at least the period from the end of the T wave to return of the LV pressure to baseline (block 712). If dispersion of relaxation is detected (block 714—yes), using, for example, the presence of multiple distinct negative peaks in the smooth derivative calculated over the period, the DHF detection likely is not reliable. Suitable dispersion detection responses (block 716) range from discarding the corresponding IVRT, to adjusting it for the influence of the non-RVC condition so that a DHF indicator can be calculated. The process then continues (block 718). However, if the smooth first derivative does not contain multiple distinct negative peaks over this period (block 714—no), dispersion of relaxation likely is not present and the DHF detection likely is reliable.

The newly calculated IVRT is used to recalculate the progression of change in the relaxation time (block 720), which upon the first pass through the method 700 is set at a default value, and thereafter is recalculated on the basis of each newly calculated ventricular isovolumetric relaxation time. If the recalculated progression of change does not exceed a threshold (block 722—no), which may be expressed as a value or as a profile as desired, DHF is indicated as absent and the process returns to block 702. However, if the recalculated progression of change in relaxation exceeds the threshold (block 722—yes), DHF is indicated and the desired DHF detection response is initiated (block 724). Suitable DHF detection responses range from merely recording the event for later inspection to adjusting a therapeutic action. The process continues after the detection response is made (block 726).

Detection of Non-Reduced Ventricular Compliance Conditions Having an Effect on IVRT Other indicia of non-RVC conditions that may have an impact on the LV pressure waveform during ventricular isovolumetric relaxation include wide T wave which is indicative of dispersion of repolarization, and wide QRS complex which is indicative of dispersion of depolarization. Functional relationships between various parameters of the LV pressure waveform and various DHF and HF conditions may be quantified in various ways, such as, for example, using characteristics that are attributable to dispersion of relaxation and DHF as mentioned above, by establishing and training functions relating parameters of the LV pressure waveform to various non-RVC conditions, by using statistical techniques to correlate waveform characteristics to various non-RVC conditions, by training neural networks using LV pressure waveforms for various non-RVC conditions, and so forth. Useful information includes absolute results as well as comparative results obtained over time.

Non-Reduced Ventricular Compliance Conditions from Waveform Parameters

One technique for identifying and quantifying non-RVC conditions that may impact IVRT is the use of various predetermined parameters and functions to calculate indicators of the non-RVC conditions from various cardiac signals. This technique involves storing in the memory 94 various pre-calculated coefficients and predetermined functions that relate the various parameters of the cardiac signals such as, for example, the LV pressure waveform during ventricular isovolumetric relaxation to the various non-RVC conditions. Measurements of LV pressure and other cardiac signals, including other mechanical-related signals as well as electrical and chemical related signals, are taken for a particular patient and preferably stored as waveform data in the memory 94. The parameters of the stored waveforms are evaluated from the waveform data, and indicators of the non-RVC conditions are calculated from the parameter values and the stored coefficients in accordance with the functions, by the microcontroller 60. As an example, consider that an indicator of dispersion of relaxation (R) may be functionally related to various parameters of the LV pressure waveform in accordance with the following:

$$R = F_r(P_1^r, \ldots, P_n^r, C_1^r, \ldots, C_n^r) \tag{1}$$

in which $F_r$ may be any of various functions, linear or non-linear, $P_1^r, \ldots, C_n^r P_n^r$ are parameters derived from LV pressure waveforms, and $C_1^r, \ldots, C_n^r$ are coefficients obtained during a training process based upon clinical data.

Figure 8:
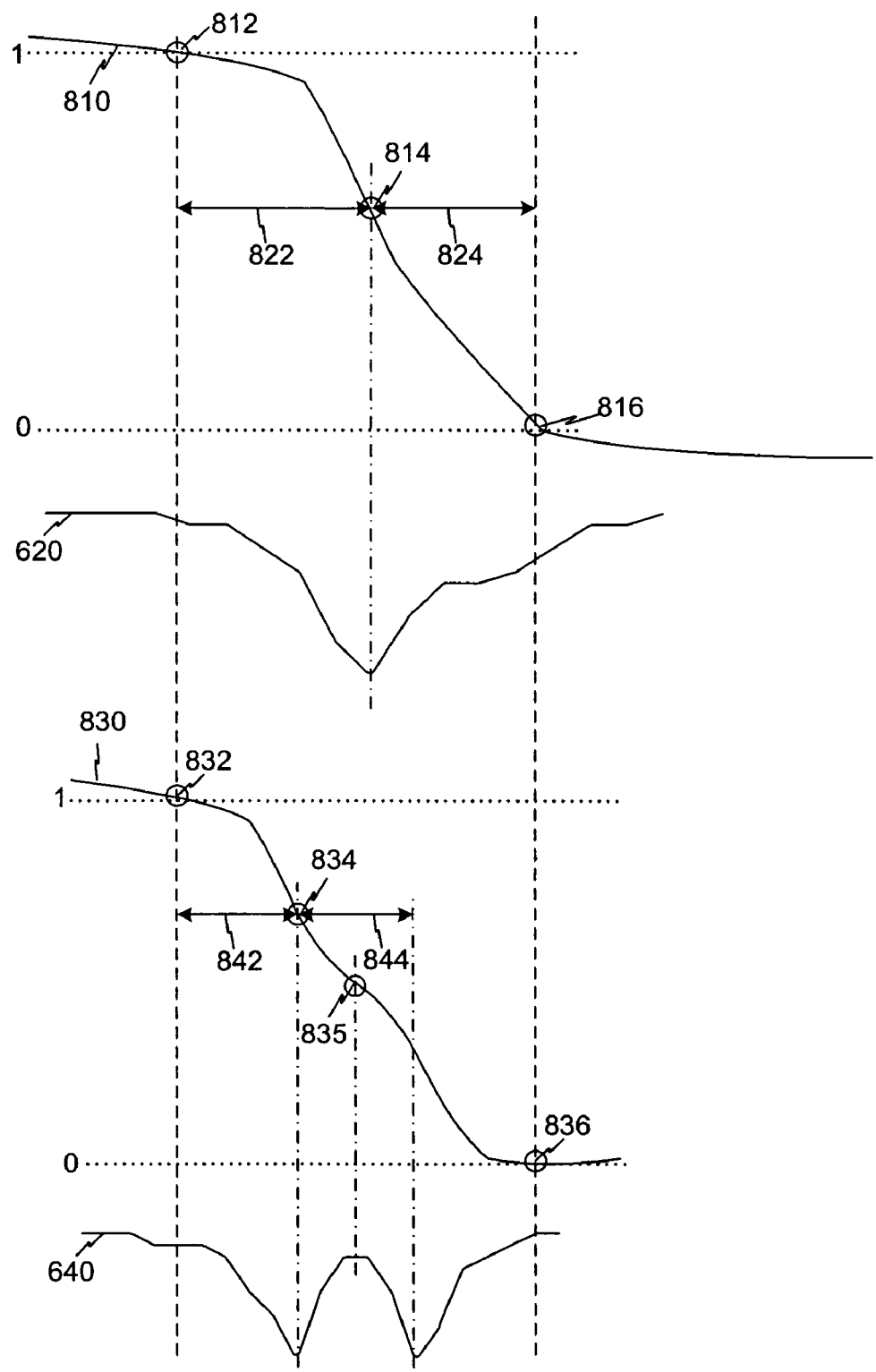
FIG. 8 is a graph showing various waveform parameters.

Assume for the purposes of explanation that the waveforms 510 and 530 (FIG. 5) are acquired clinically, and are known to correspond respectively to a healthy heart and a heart suffering from dispersion of relaxation. FIG. 8 is a graph showing sections 810 and 830 of respectively the waveforms 510 and 530 (FIG. 5) over the period of ventricular isovolumetric relaxation, normalized in amplitude at the end of the T wave (812, 832) and at the threshold value (816, 836), and normalized in time. The traces are scaled horizontally and vertically to eliminate gain differences between the different patients.

The smooth derivative traces 620 and 640 corresponding to the waveform sections 810 and 830 are also shown. Various parameters for dispersion of relaxation are identified on the scaled waveforms, and illustratively include (a) the scaled time from the start of ventricular isovolumetric relaxation to the most rapid pressure change, shown at 822 for trace 810, and shown at 842 for trace 830; (b) the scaled time of any hesitation in the rapid pressure change, which is absent from the trace 810 but is shown at 844 for trace 830; (c) the amplitude at the first point of rapid pressure change, shown at 814 for trace 810 and at 834 for trace 830; and (d) the amplitude at the minimum between two negative peaks of the smooth first derivative, which is absent from trace 810 and is shown at 835 for trace 830. Other parameters of possible interest may include widths of the ventricular isovolumetric relaxation waveform at selected points along the vertical axis, ratios of individual waveform pressure amplitudes at selected points along the horizontal axis and the amplitude of the waveform, the rise time or time elapsed from the start of the waveform to a selected point along the vertical axis, waveform slope characteristics, and other shape characteristics.

Once the parameters are selected, coefficients corresponding to the parameters are calculated. The coefficients represent the relationship between a particular parameter set and a particular non-RVC condition to be determined from the particular parameter set. The coefficients are initially ascertained using results from clinical tests upon patients having known non-RVC conditions. The implantable cardiac device receives the sensed pressure waveform data, and the various parameters are evaluated from the sensed pressure waveform data. Coefficients are calculated using the values of the selected parameters and values of indicators of the non-RVC conditions. Preferably, many patients are clinically tested to ascertain the coefficients. Training may be performed with patients from many different patient groups such as age, weight, smoking, and other risk factors, or may be performed within specialized patient groups. Once obtained, the coefficients are stored for use in detecting and/or monitoring these non-RVC conditions in patients, without the need for prior diagnosis.

Table 1 below lists various illustrative parameters for the simple sum of products function of Equation 1, which are useful for calculating dispersion of relaxation.

TABLE 1

| PARAMETER | DESCRIPTON |
|---|---|
| $p_1^d$ | Maximum slope of the time domain pressure signal ($dPdt_{max}$) |
| $p_2^d$ | Number of peaks from the smooth derivative |
| $p_3^d$ | Integral of the curve between |

It will be appreciated that many other different parameters may be used in addition to or in lieu of some of or all of these parameters, including, for example, various ratios, rise times, amplitudes, elapsed time between two waveform characteristics, peaks, derivatives, waveform widths at particular amplitudes, and so forth.

Detection of Non-Reduced Ventricular Compliance Conditions from Statistical Analysis Various well known statistical techniques may be used to identify and quantify non-RVC conditions that may impact IVRT.

In one statistical technique, the waveform data from a training set is pre-processed to reduce inter-patient variation. The pre-processed waveform data are then dimensionally reduced into an informative set of principal components which describe most of the variance of the training data set using Principal Component Analysis. Next, the principal components which contain diagnostically relevant information for various heart conditions are selected using an unpaired, one-sided Student t-test, and finally a classification algorithm based on logistic discrimination is developed using these diagnostically relevant principal components.

In another statistical technique, heart electrical variables such as the width of the QRS complex, and the width and dispersion of the T wave may be correlated with IVRT using the Student t-test and linear regression analysis.

Avoidance of Complications from Non-Reduced Ventricular Compliance Conditions

Figure 9:
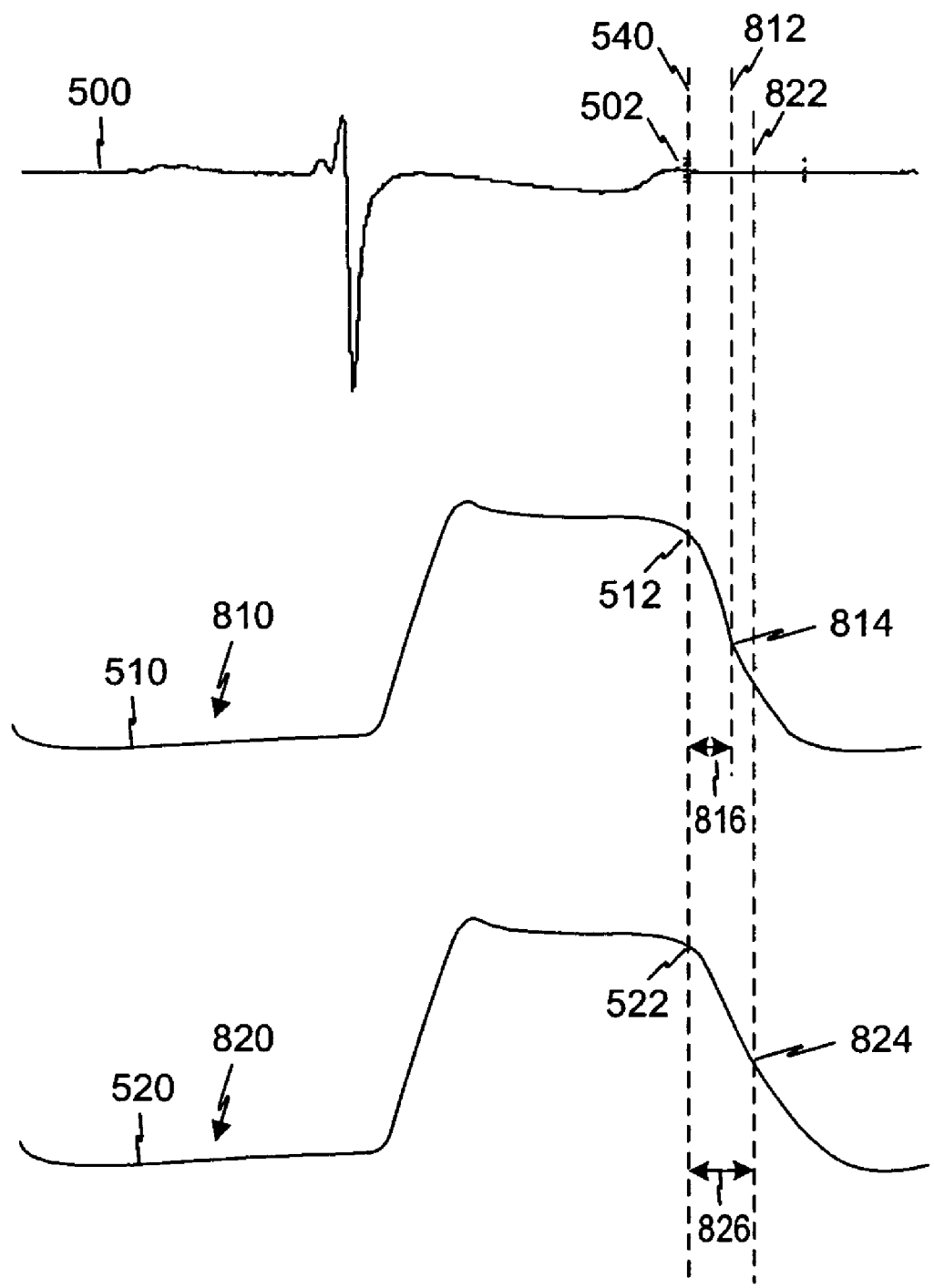
FIG. 9 is a graph showing waveforms for a right ventricular tip ("RVT") EGM and for left ventricular ("LV") pressure to illustrate an alternative method for measuring an isovolumetric relaxation interval.

FIG. 9 is a graph showing waveforms for a right ventricular tip ("RVT") EGM and for left ventricular ("LV") pressure to illustrate an alternative method for measuring an isovolumetric relaxation interval. Similar to FIG. 5, the waveform 500 is a right ventricular tip ("RVT") EGM, and the waveform 510 and 520 are left ventricular ("LV") pressure waveforms correlated in time for a complete cardiac cycle. The vertical line 540 shows the starts 512 and 522 of the rapid decline in LV pressure after aortic valve closure, or IVRT, for the waveforms 510 and 520 respectively. The points 512 and 522 may be determined by any of various techniques, including the end 502 of the T wave, detection of the dicrotic notch from waveform analysis of the aortic pressure, detection of the heart sounds S2 from an acoustic sensor, detection of a discontinuity or blip in a left atrial pressure measurement, and waveform analysis of the LV pressure to detect a change from a slow decline to a rapid decline. However, the end of IVRT is determined differently than described with reference to FIG. 5.

Rather than attempting to calculate IVRT by determining the end of IVRT, this technique uses a new parameter IVRT-F (fractional). IVRT-F may be thought of as a point on the waveform at which the LV pressure amplitude declines to a fraction of the pressure at the beginning of isovolumetric relaxation, illustratively one half of the LV pressure at the beginning of isovolumetric relaxation which is seen at point 814 for the waveform 510, and at point 824 for the waveform 520. The amplitude 814 is obtained by subtracting from the LV pressure at point 512 ($LVP_{512}$) a pre-baseline LV pressure value determined generally at point 810 in the waveform 510 ($LVP_{810}$) and dividing by two (where the fraction is one-half), or $$LVP_{814} = (LVP_{512} - LVP_{810})/2 \qquad (2)$$

Similarly, the amplitude 824 is obtained by subtracting from the LV pressure at point 522 ($LVP_{522}$) a pre-baseline LV pressure value determined generally at point 820 in the waveform 520 ($LVP_{820}$) and dividing by two (where the fraction is one-half), or $$LVP_{824} = (LVP_{512} - LVP_{820})/2 \qquad (3)$$

The parameter IVRT-F 816 for the waveform 510 is obtained simply by subtracting the time 540 at which $LVP_{512}$ occurs from the time 812 at which $LVP_{814}$ occurs. Similarly, the parameter IVRT-F 826 for the waveform 520 is obtained simply by subtracting the time 540 at which $LVP_{512}$ occurs from the time 822 at which $LVP_{824}$ occurs. For DHF patients whose IVRT prolongs, as is evident in waveform 520, the parameter IVRT-F prolongs as well, as is evident from a comparison of the relatively short IVRT-F 816 to the relatively long IVRT-F 826, thus showing that IVRT-F it a useful indicator for DHF detection.

An advantage of using IVRT-F over other techniques is that sometimes mitral valve opening occurs before the LV pressure completely returns to the baseline, thereby complicating the IVRT determination for these patients. This condition typically is found in some patients whose left atrial pressure is elevated. Using IVRT-F eliminates this potential complication by measuring the IVRT-F parameter before mitral valve abruptly opens, since the mitral valve is unlikely to open before the LV pressure reaches one-half of its value at point 512.

Other waveform parameters may also be used as indicators of IVRT. The part of the LV pressure waveform of greatest interest for these parameters is the part from start of IVRT to before earliest probable mitral valve opening. Suitable parameters include waveform slope over a fixed period of time from start of IVRT, peak slope over a particular period of time or until decline of the LV pressure to a particular value (smooth first derivative being preferred to instantaneous first derivative to avoid noise problems), and so forth.

Each of the techniques described herein may be augmented by the use of other techniques, including other techniques described herein, to provide multiple IVRT measurements from which the most accurate may be selected or to obtain mutual validation.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A method of monitoring a patient for diastolic heart failure with an implanted cardiac device, comprising:
   obtaining with the implanted cardiac device a waveform indicative of left ventricular pressure of the patient during an early part of isovolumetric relaxation;
   calculating an indication of dispersion of relaxation from the waveform;
   calculating a parameter from the waveform that is indicative of diastolic heart failure;
   adjusting the parameter as a function of the indication of dispersion;
   calculating an indication of diastolic heart failure from the adjusted parameter; and
   adjusting a therapeutic action in response to the indication of diastolic heart failure and the indication of dispersion of relaxation.

2. The method of claim 1 wherein calculating a parameter that is an indication of diastolic heart failure from the waveform comprises calculating a time from a first amplitude level of the waveform to a second amplitude level of the waveform less than the first amplitude level.

3. The method of claim 1 wherein calculating an indication of dispersion of relaxation from the waveform comprises calculating slope of the waveform over a fixed period of time from start of isovolumetric relaxation, or a maximum slope of the LV waveform over a particular period of time, or maximum slope of the LV waveform until decline of the LV pressure to a particular value.

4. The method of claim 1 wherein calculating a parameter from the waveform that is indicative of diastolic heart failure comprises calculating the isovolumetric relaxation time.

5. A method of monitoring a patient for diastolic heart failure with an implanted cardiac device, comprising:
   obtaining with the implanted cardiac device at least one cardiac signal indicative of cardiac activity of the patient;
   calculating from the cardiac signal in the implanted cardiac device a ventricular isovolumetric relaxation time;
   obtaining an indication of a heart condition that is capable of influencing the ventricular isovolumetric relaxation time, other than reduced ventricular compliance;
   calculating an indication of diastolic heart failure from the ventricular isovolumetric relaxation time and the heart condition indication; and
   adjusting a therapeutic action in response to the indication of diastolic heart failure.

6. The method of claim 5 further comprising reporting the ventricular isovolumetric relaxation time to an external device, wherein the heart condition indication is obtained from the external device and the diastolic heart failure calculating step is performed by the external device.

7. The method of claim 5 wherein the heart condition indication and the diastolic heart failure are calculated by the implantable cardiac device.

8. The method of claim 5 further comprising reporting the indication of diastolic heart failure to an external device.

9. The method of claim 5 wherein the cardiac signal obtaining step comprises detecting left ventricle pressure of the patient with the cardiac device.

10. The method of claim 5 wherein the diastolic heart failure indication calculating step comprises evaluating diastolic heart failure from a prior progression of change in relaxation time, in addition to the ventricular isovolumetric relaxation time and the heart condition indication.

11. A method of monitoring a patient for diastolic heart failure with a cardiac device implanted in the patient, comprising:
    obtaining with the implanted cardiac device a T wave ending time for a heart beat from an intracardiac electrogram;
    obtaining with the implanted cardiac device a return to baseline time of left ventricle pressure for the heart beat from a left ventricle pressure sensor;
    deriving a ventricular relaxation time for the heart beat from the T wave ending time and the return to baseline time;
    evaluating diastolic heart failure from the derived ventricular relaxation time; and
    adjusting a therapeutic action in response to the evaluation of diastolic heart failure.

12. The method of claim 11 wherein the diastolic heart failure evaluating step comprises evaluating diastolic heart failure from a prior progression of change in relaxation time, in addition to the calculated ventricular relaxation time.

13. The method of claim 11 further comprising:
    detecting absence of a heart condition having a possible influence on the ventricular relaxation time, other than reduced ventricular compliance;
    wherein the diastolic heart failure evaluating step is performed in response to the heart condition absence detecting step.

14. The method of claim 11 further comprising triggering the return to baseline time obtaining step from the T wave ending time obtaining step.

15. The method of claim 11 wherein the evaluating step comprises:
    comparing the derived ventricular relaxation time to a threshold condition; and indicating diastolic heart failure when the derived ventricular relaxation time deviates in a predetermined manner from the threshold condition.

16. The method of claim 11 further comprising:

acquiring an RVT-EGM measurement from the patient with the cardiac device, the T wave ending time being obtained from the RVT-EGM measurement; and assigning a predetermined threshold value as the baseline.

17. An implantable cardiac device comprising:

means for obtaining a T wave ending time from an intracardiac electrogram;

means for obtaining a return to baseline time of left ventricle pressure from a left ventricle pressure sensor;

means for deriving a ventricular relaxation time from the T wave ending time and the return to baseline time; and means for evaluating diastolic heart failure from the calculated ventricular relaxation time.

18. An implantable cardiac device comprising:

means for obtaining a waveform indicative of left ventricular pressure of the patient during an early part of isovolumetric relaxation, prior to a mitral valve opening;

means for determining a parameter of the waveform obtained during the early part of isovolumetric relaxation; and means for calculating an indication of diastolic heart failure from the waveform parameter.

* * * * *